United States Patent [19]

Konwitz

[11] Patent Number: 5,364,391

[45] Date of Patent: Nov. 15, 1994

[54] LASER BEAM DELIVERY SYSTEM

[75] Inventor: Ellie Konwitz, Ramat Gan, Israel

[73] Assignee: Laser Industries Ltd., Neve Sharet, Israel

[21] Appl. No.: 70,816

[22] Filed: Jun. 3, 1993

[30] Foreign Application Priority Data

Jun. 3, 1992 [IL] Israel ........................... 102083

[51] Int. Cl.$^5$ ............................... A61B 17/36
[52] U.S. Cl. ........................ 606/16; 606/13; 606/17
[58] Field of Search .................... 606/7, 13–17, 606/27, 28; 607/88, 89

[56] References Cited

U.S. PATENT DOCUMENTS

| | | | |
|---|---|---|---|
| 4,538,609 | 9/1985 | Takenaka et al. | 606/16 |
| 4,608,980 | 9/1986 | Aihara | 606/16 |
| 4,693,244 | 9/1987 | Daikuzono | 606/16 |
| 4,940,411 | 7/1990 | Vassiliadis et al. | 606/16 |
| 5,037,421 | 8/1991 | Boutacoff et al. | 607/89 |

Primary Examiner—Stephen C. Pellegrino
Assistant Examiner—Michael Peffley
Attorney, Agent, or Firm—Benjamin J. Barish

[57] ABSTRACT

A laser beam delivery system includes a fiber cord assembly connectable to a laser beam source; a probe connector assembly connectable at one end to the fiber cord assembly and having a socket at its opposite end for receiving, in a quickly attachable/detachable manner, a fiber probe to deliver the laser beam to a working site; and a fiber probe for insertion into the socket.

16 Claims, 3 Drawing Sheets

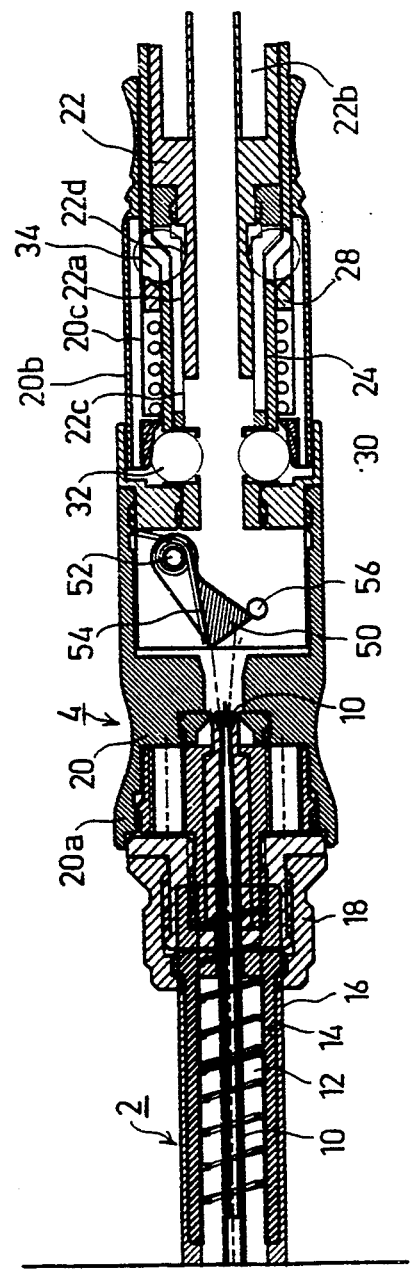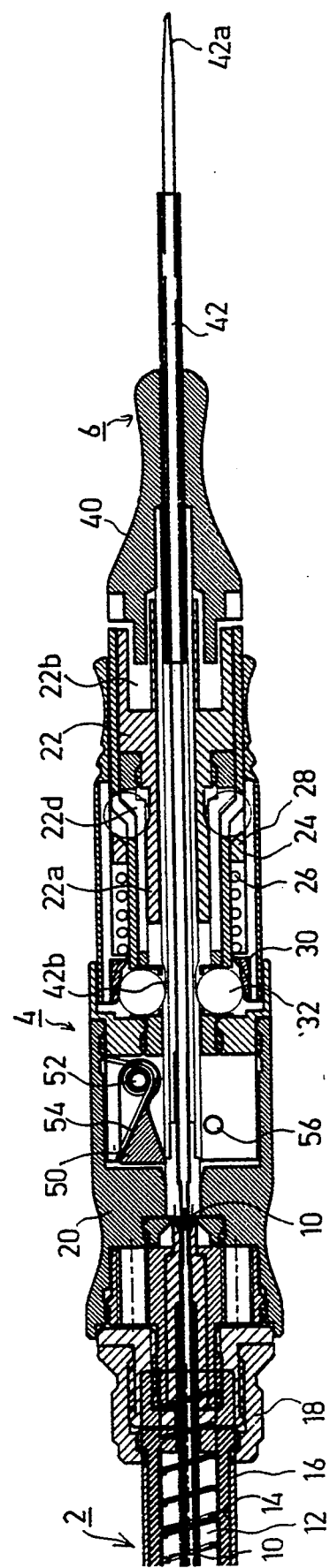
FIG. 1
FIG. 2

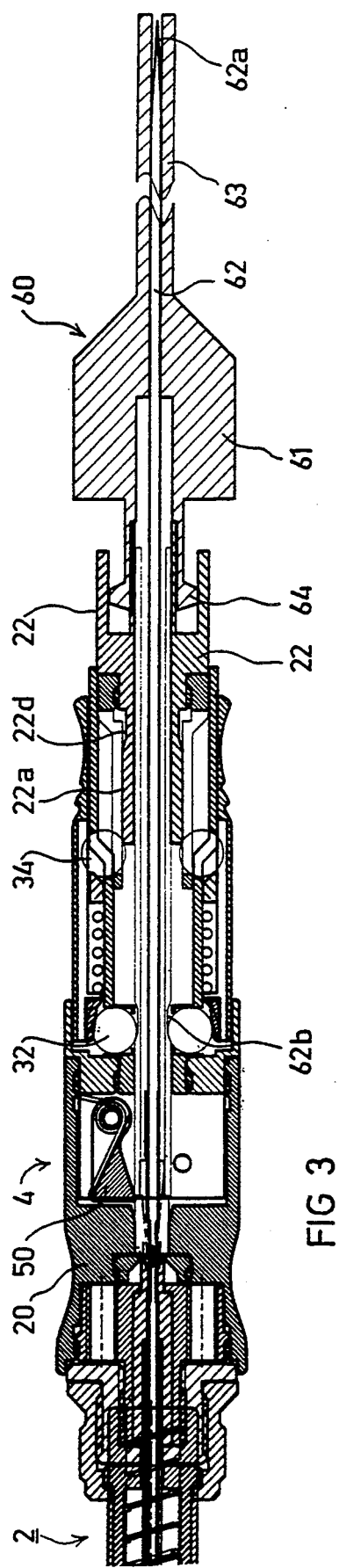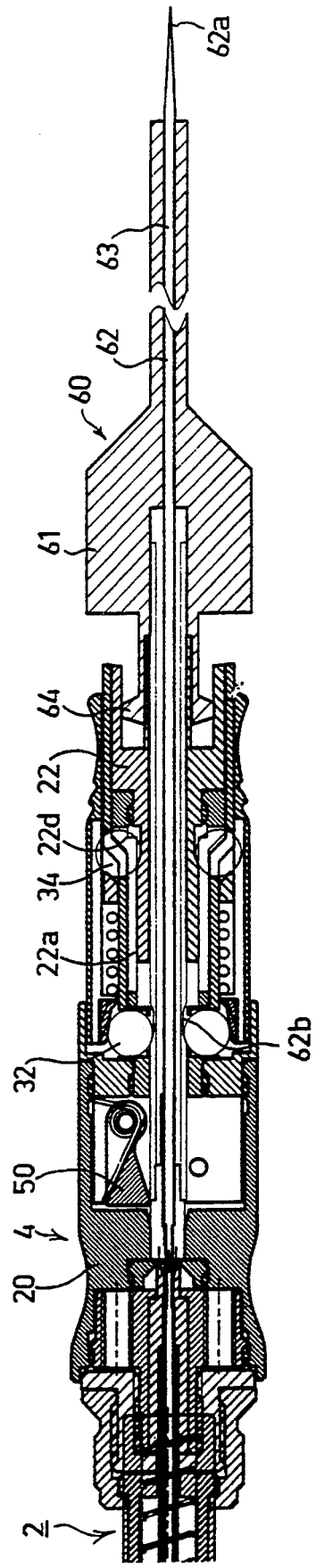

LASER BEAM DELIVERY SYSTEM

FIELD AND BACKGROUND OF THE INVENTION

The present invention relates to a laser beam fiber delivery system, and particularly to one useful in surgical lasers for delivering a laser beam to a working site.

The invention is especially useful in surgical lasers of the Nd:YAG laser type including optical fibers for delivering the laser beam to the working site. The conventional laser beam delivery system of this type includes a single fiber cord, of about 3-4 meters in length, connected between the laser beam source and the working site. However, such a single fiber cord is generally not reusable, and therefore a substantial expense is involved in disposing it after a single use. Moreover, it is frequently necessary, for different surgical procedures and effects, to use different types of fiber tips, such as pointed, hemispherical or flat tips, sometimes for contact, and other times for non-contact with the tissue at the working site. For example, a surgical procedure may require first a contact-type tip for incising tissue, and then a non-contact-type tip for coagulation of the tissue. A change-over from one type of tip to another is not only expensive because of the need to replace the complete fiber cord, but is also inconvenient and time-consuming.

It would therefore be highly desirable, particularly in a surgical laser, to provide a laser beam delivery system having advantages in the above respects.

OBJECTS AND BRIEF SUMMARY OF THE INVENTION

According to the present invention, there is provided a laser beam delivery system comprising: a fiber cord assembly connectable to a laser beam source; a probe connector assembly connectable at one end to the fiber cord assembly and having a socket at its opposite end for receiving, in a quickly attachable/detachable manner, a fiber probe to deliver the laser beam to a working site; and a fiber probe for insertion into the socket.

It will thus be seen that, in such a laser beam delivery system, the fiber cord assembly and the probe connector assembly can both be reused, and only the fiber probe needs to be replaced after each use. Such a system would normally include a plurality of different types of fiber probes, having different types of working tips, to permit the surgeon to quickly replace one probe by another according to the surgical effect desired.

According to additional features in the preferred embodiments of the invention described below, the probe connector assembly further includes a mechanical shutter normally biased to a blocking position to block the passage of the laser beam, but automatically movable to an unblocking position upon the insertion of the fiber probe into the socket.

According to further features, the fiber probe may include a fingerpiece graspable by the user and insertable at one end into the socket, and a working fiber extending through the fingerpiece and having a working tip projecting through its opposite end. In one type of fiber probe described, the fingerpiece is fixed to the working fiber. A second type of fiber probe is described wherein the fingerpiece is slidable with respect to the working fiber and includes a protective sheath which encloses the working fiber in an extended position of the fingerpiece, and exposes the working fiber in a retracted position of the fingerpiece.

According to yet additional features in another described embodiment, the probe connector assembly further includes, at the end thereof connectable to the laser beam source, a lens system for imaging the laser beam onto the input end face of the fiber probe with an image covering less than the complete area of the end face. In the latter embodiment, the lens system is carried by an inner sleeve receivable within an outer sleeve of the probe connector assembly, to permit the probe connector assembly to be separated from the lens system and autoclaved.

Further features and advantages of the invention will be apparent from the description below.

BRIEF DESCRIPTION OF THE DRAWINGS

The invention is herein described, by way of example only, with reference to the accompanying drawings, wherein:

FIGS. 1 and 2 are longitudinal section views illustrating one form of laser beam delivery system in accordance with the present invention, FIG. 1 illustrating the system without a fiber probe attached, and FIG. 2 illustrating the system with a fiber probe attached;

FIGS. 3 and 4 are views similar to that of FIG. 2 but showing another type of attached fiber probe in two different positions.

DESCRIPTION OF PREFERRED EMBODIMENTS

Figure 5:
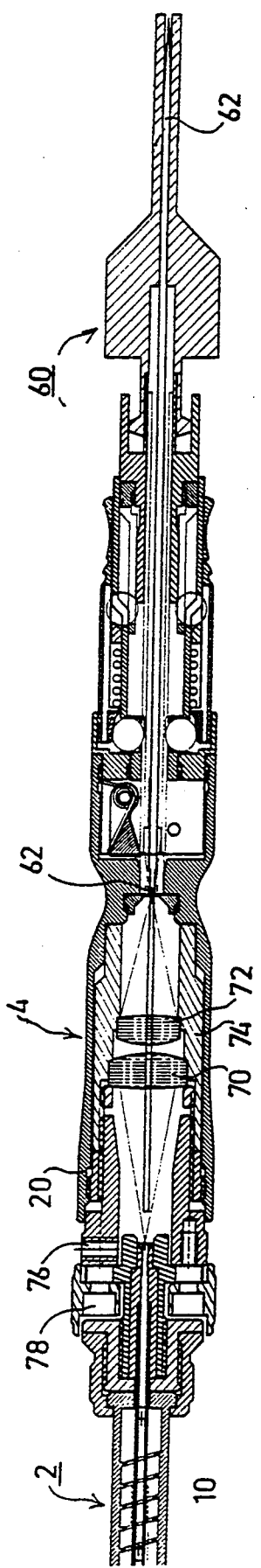
FIG. 5 is a similar view to that of FIG. 3 but including a lens system for imaging the laser beam on the end face of the fiber probe.

The Embodiment of FIGS. 1 and 2

The laser beam delivery system illustrated in FIGS. 1 and 2 is particularly useful in surgical lasers for delivering an Nd:YAG laser beam to a working site. The illustrated system comprises a fiber cord assembly, generally designated 2, connectable to a laser beam source (not shown); and a probe connector assembly, generally designated 4, connectable at one end to the fiber cord assembly 2 and adapted to receive a fiber probe 6 (FIG. 2) in its opposite end for delivering the laser beam to the working site. FIG. 2 illustrates one form of fiber probe 6 which may be used, but it will be appreciated that a system would normally include a plurality of different types of probes, permitting them to be quickly changed according to the requirements for any particular operating procedure.

The fiber cord assembly 2 may be of a known construction, including a central fiber core 10 enclosed within a flexible cable. Such a flexible cable includes a flexible protective tube 12, a plastic cover 14, and an outer metal jacket 16. The flexible cable is attached to the probe connector assembly 4 by a threaded fitting 18 such that the fiber core 10 is flush with the end of the fitting, as shown at 10' in FIGS. 1 and 2. Such an arrangement provides abutting contact between the fiber core 10 and the working fiber in the fiber probe to be connected to the cord assembly by the probe connector assembly 4.

The probe connector assembly 4 includes an outer sleeve 20 having a section 20a at one end adapted to be coupled by fitting 18 to the fiber cord assembly 2, and a second section 20b at its opposite end carrying a socket 22 for receiving the fiber probe 6 (FIG. 2). Sleeve section 20b is slidable with respect to sleeve section 20a. Socket 22 is formed at one end with a sleeve 22a, slideably received within the probe connector assembly 4, and with an annular recess 22b at its opposite end for receiving the fiber probe 6.

The probe connector assembly 4 further includes an intermediate sleeve 24 which is fixed to section 20b of the outer sleeve 20. A helical spring 26 is located on the outer surface of the intermediate sleeve 24, between a ring 28 and a ball cage 30 containing an annular array of balls 32. Balls 32 serve as a releasable retainer means for releasably retaining the fiber probe 6 in the probe connector assembly 4, as will be described more particularly below.

The intermediate sleeve 24 carries a second annular array of balls 34, which balls serve additional functions as will also be described below.

The fiber probe 6 illustrated in FIG. 2 includes a fingerpiece 40 graspable by the user for insertion into the annular recess 22b of socket 22, and a working fiber 42 projecting through the end of the fingerpiece and formed with a working tip 42a. The working fiber 42 is further formed with an annular recess 42b at its opposite end, cooperable with the annular array of balls 32. These balls, when seated in recess 42b, releasably retain the working fiber 42 of the fiber probe 6 within the probe connector assembly 4.

The annular array of balls 34 carried by the intermediate sleeve 24, acting on ring 28 and spring 26, bias the ball cage 30 in the direction to press the balls 32 into the annular recess 42b of the working fiber 42. Sleeve section 20b is manually moved rightwardly to release the balls from the annular recess. Balls 34 also serve as key means for preventing the rotation of socket 22, and the fiber probe 6 carried thereby. This is particularly important when the fiber probe 6 includes working fibers having curved or angled tips. For this keying function, the balls 34 are received within axially-extending grooves 22c formed in the sleeve section 22a of socket 22, and also in axially-extending grooves 20a formed in the outer sleeve 20.

Balls 34 also cooperate with an annular recess 22d formed in sleeve section 22a of the socket 22, for releasably retaining the socket in a selected axial position, as will be described more particularly below with respect to FIGS. 3 and 4.

The probe connector assembly 4 further includes a mechanical shutter 50 of triangular configuration and pivotally mounted to a pin 52. Shutter 50 is normally biased by a spring 54 to a blocking position against a fixed pin 56, as shown in FIG. 1, but is automatically pivotal to an unblocking position upon the insertion of a fiber probe, such as shown at 6 in FIG. 2, or at 60 in FIGS. 3 and 4.

FIG. 1 illustrates the condition of the probe connector assembly 4 when a fiber probe (e.g. 6, FIG. 2) is not attached to it. Thus, in this position, shutter 50 is pivoted by spring 54 to its blocking position to block the passage of a laser beam from the fiber core 10 of the fiber cord assembly 2, should the laser be accidentally operated at that time.

When a fiber probe is inserted into the probe connector assembly 4, as shown by the insertion of fiber probe 6 in FIG. 2, the working fiber 42 of the probe is passed through the probe connector assembly 4 until it abuts against the end face of the fiber core 10 in the fiber cord assembly 2. During this passage of the working fiber 42 through the probe connector assembly 4, it engages the inclined surface of shutter 50 and pivots it to its unblocking position, as shown in FIG. 2. When the fiber probe has been fully inserted into the connector assembly, balls 32 seat in the annular recess 42b of the working fiber 42, thereby releasably retaining the fiber probe in the connector assembly. In addition, balls 34 receivable within the axial grooves 22c of socket 22, and grooves 20a of outer sleeve 20, prevent rotation of the fiber probe with respect to the connector assembly 4.

It will thus be seen that the illustrated system permits fiber probes, such as shown at 6 in FIG. 2, to be quickly attached and detached, as may be required during a surgical procedure. In addition, the probe connector assembly 4, as well as the fiber cord assembly 2, can be reused, and only the probe 6 is disposable after a single use, thereby decreasing the costs in using the illustrated system.

The Embodiment of FIGS. 3 and 4

The probe connector assembly 4 illustrated in FIGS. 1 and 2 may thus be used with many different types of probes. FIGS. 3 and 4 illustrate the use of this assembly in a probe 60 which includes a protective sheath for protecting the working fiber against contamination or breakage when not in use.

Thus, as shown in FIGS. 3 and 4, the fiber probe 60 also includes a fingerpiece 61 graspable by the user, for insertion into the probe connector assembly 4 and a working fiber 62 having a working tip 62a. In this case, however, the fingerpiece 61 is not fixed to the working fiber 62, but rather is slidable with respect to it. In addition, the fingerpiece 61 includes a sheath 63 which, in the extended position of the fingerpiece (FIG. 3), encloses the working fiber 62 to protect it against contamination or breakage, but which is movable to a retracted position (FIG. 4) to expose the working tip of the fiber for surgical use at the working site.

In the construction illustrated in FIGS. 3 and 4, socket 22 is formed with a Luer lock cooperating with pin 64 at the inserted end of the fiber probe 60, to permit the fiber probe to be conveniently attached and detached with respect to the probe connector assembly 4. A similar Luer lock arrangement may also be used in the construction illustrated in FIGS. 1 and 2.

The assembly of FIGS. 3 and 4 is otherwise constructed, and is used, in the same manner as described above with respect to FIGS. 1 and 2. When the fiber probe 60 is used, however, the probe connector assembly 4 permits the fingerpiece 61, and particularly its sheath 63, to be moved either to its extended position (FIG. 3), to protect the working fiber 62 against contamination or breakage, or to its retracted position (FIG. 4) exposing the working fiber for use. Thus, when the sheath 63 is to be moved to its extended, protective position (FIG. 3), the fingerpiece 61 is slid (rightwardly) until the balls 34 seat against the end of the inner sleeve 22a of socket 22; when the sheath 63 is to be retracted to its retracted position (FIG. 4), fingerpiece 61 is slid (leftwardly) until the balls 34 seat in the annular recess 22d formed in the inner sleeve 22a of socket 22.

Balls 34 thus determine the retracted and extended position of sheath 63. They also serve the other functions described above with respect to FIGS. 1 and 2: they urge balls 32 into the annular recess 62b of the working fiber 62, to firmly retain the working fiber in place; they also move within the axial grooves 22c in the inner sleeve 22a, and groove 20a of outer sleeve 20, to prevent rotation of the fiber probe.

The Embodiment of FIG. 5

FIG. 5 illustrates a system similar to that of FIGS. 3 and 4, except that the probe connector assembly 4 in the system of FIG. 5 includes a lens system for imaging the laser beam, exiting from the fiber core 10 of the fiber cord assembly 2, onto the end face of the working fiber 62 of the fiber probe 60.

Thus, as shown in FIG. 5, the probe connector assembly 4 includes a pair of lenses 70, 72. These lenses are held within a sleeve 74 received within the outer sleeve 20 of the probe connector assembly 4. The two lenses 70, 72 are designed to image the laser beam exiting from the fiber core 10 of the fiber cord assembly 2 onto the end face of the working fiber 62 of the fiber probe 60, but to cover only 80% of the surface of the end face of the latter fiber. The reason for this is to accommodate any slight misalignment and to prevent the laser beam from burning the outer cladding of the working fiber in case of a slight misalignment.

The fiber core 10 in the fiber cord assembly 2 is aligned along one orthogonal axis by locking screw 76, along the second axis by a similar locking screw (not shown), and along the third orthogonal axis by locking screw 78, so that once aligned, realignment is usually not necessary when substituting fiber probes.

In the arrangements illustrated in FIGS. 1-4, the probe connector assembly 4 is autoclavable after detaching the disposable fiber probe, so that the same assembly can be reused after sterilization with different pre-sterilized fiber probes. In the arrangement illustrated in FIG. 5, the lenses 70, 72 are not autoclavable, and therefore when the probe connector assembly 4 is to be autoclaved for reuse, it is removed from the inner sleeve 74 carrying the lenses 70, 72, before being autoclaved.

While the invention has been described with respect to several preferred embodiments, it will be appreciated that these are set forth merely for purposes of example, and that many other variations, modifications and applications of the invention may be made.

What is claimed is:

1. A laser beam delivery system adapted to deliver a laser beam, comprising:
    a fiber cord assembly connectable at one end to a laser beam source;
    a probe connector assembly connected at one end to said fiber cord assembly and having a socket at its opposite end;
    a fiber probe received in said socket in a quickly attachable/detachable manner to deliver a laser beam from said source to a working site;
    and a mechanical shutter within said probe connector assembly normally biased to a blocking position to block the passage of the laser beam, but movable to an unblocking position upon the insertion of the fiber probe into said socket.

2. The system according to claim 1, wherein said fiber probe includes a fingerpiece graspable by the user and insertable at one end into said socket, and a working fiber extending through said fingerpiece and having a working tip projecting through its opposite end.

3. The system according to claim 2, wherein said fingerpiece is slidable with respect to said working tip and includes a protective sheath which encloses the working fiber in an extended position of the fingerpiece, and exposes the working fiber in a retracted position of the fingerpiece.

4. The system according to claim 3, wherein said socket is slidable in the probe connector assembly to permit the fingerpiece, when inserted therein, to be moved to its extended or retracted positions, said probe connector assembly further including retainer means for releasably retaining the socket in both said positions.

5. The system according to claim 4, wherein said retainer means comprises an annular array of balls spring-urged into an annular recess formed in said working fiber.

6. The system according to claim 4, wherein said probe connector assembly further includes an outer sleeve, an inner sleeve slidable with respect to said outer sleeve and carrying the socket for receiving the fingerpiece of the fiber probe, and key means between said sleeves to prevent rotation of the inner slidable sleeve, and the working fiber carried thereby, with respect to said outer sleeve.

7. The system according to claim 6, wherein said key means comprises an annular array of balls carried by an intermediate sleeve and movable within axially-extending grooves in said inner sleeve.

8. The system according to claim 7, wherein said inner sleeve is formed with an annular recess for receiving said annular array of balls in the retracted position of the sheath.

9. The system according to claim 1, wherein said probe connector assembly further includes, at the end thereof connectable to the laser beam source, a lens system for imaging the laser beam onto an input end face of the fiber probe with an image covering less than the complete area of said input end face.

10. The system according to claim 9, wherein said lens system is carried by an inner sleeve receivable within an outer sleeve of the probe connector assembly, to permit the probe connector assembly to be separated from the lens system and autoclaved.

11. A laser beam delivery system adapted to delivery a laser beam, comprising:
    a fiber cord assembly connectable to a laser beam source;
    a probe connector assembly connected at one end to said fiber cord assembly and having a socket at its opposite end;
    and a fiber probe received in said socket in a quickly attachable/detachable manner to deliver a laser beam from said source to a working site;
    said fiber probe including a fingerpiece graspable by the user and insertable at one end into said socket, and a working fiber extending through said fingerpiece and having a working tip projecting through its opposite end;
    said fingerpiece being slidable with respect to said working tip and including a protective sheath which encloses the working fiber in an extended position of the fingerpiece, and exposes the working fiber in a retracted position of the fingerpiece.

12. The system according to claim 11, wherein said probe connector assembly further includes a mechanical shutter normally biased to a blocking position to block the passage of the laser beam, but automatically movable to an unblocking position upon the insertion of the fiber probe into said socket.

13. The system according to claim 11, wherein said socket is slidable in the probe connector assembly to permit the fingerpiece, when inserted therein, to be moved to its extended or retracted positions, said probe connector assembly further including retainer means for releasably retaining the socket in both said positions.

14. The system according to claim 3, wherein said retainer means comprises an annular array of balls spring-urged into an annular recess formed in said working fiber.

15. A laser beam delivery system, comprising:
a laser beam source;
a fiber cord assembly connected at one end to said laser beam source;
a probe connector assembly connected at one end to said fiber cord assembly and having a socket at its opposite end;
a fiber probe received in said socket in a quickly attachable/detachable manner to deliver a laser beam from said source to a working site;
and a mechanical shutter within said probe connector assembly normally biased to a blocking position to block the passage of the laser beam, but engageable by a working fiber carried by the fiber probe to be automatically moved to an unblocking position upon the insertion of the fiber probe into said socket;
said probe connector assembly further including, at the end thereof connectable to the laser beam source, a lens system for imaging the laser beam onto an input end face of the fiber probe with an image covering less than the complete area of said input end face.

16. The system according to claim 15, wherein said lens system is carried by an inner sleeve receivable within an outer sleeve of the probe connector assembly, to permit the probe connector assembly to be separated from the lens system and autoclaved.

* * * * *